US006803183B2

(12) United States Patent
Amoureux et al.

(10) Patent No.: US 6,803,183 B2
(45) Date of Patent: Oct. 12, 2004

(54) METHOD FOR REMOVING PYROGENS FROM PLASMA AND BLOOD FOR TREATMENT OF SEPTIC SHOCK

(75) Inventors: Marie-Claude Amoureux, San Diego, CA (US); Edit Hegyi, Valley Center, CA (US); Peter Grandics, Rancho Santa Fe, CA (US); Susan Szathmary, Rancho Santa Fe, CA (US)

(73) Assignee: Clarigen, Inc., Carlsbad, CA (US)

( * ) Notice: Subject to any disclaimer, the term of this patent is extended or adjusted under 35 U.S.C. 154(b) by 93 days.

(21) Appl. No.: 10/198,774

(22) Filed: Jul. 18, 2002

(65) Prior Publication Data

US 2004/0014022 A1 Jan. 22, 2004

(51) Int. Cl.$^7$ .............................. A01N 1/02; B01D 1/00; B01D 11/00
(52) U.S. Cl. .............................. 435/2; 210/501; 210/633
(58) Field of Search .............................. 435/2; 210/501, 210/633

(56) References Cited

U.S. PATENT DOCUMENTS

| 4,576,928 A | 3/1986 | Tani et al. |
| 5,403,917 A | 4/1995 | Boos et al. |
| 5,466,377 A | 11/1995 | Grandics et al. |
| 5,571,415 A | 11/1996 | Clikeman et al. |
| 5,679,775 A | 10/1997 | Boos et al. |
| 5,980,479 A | 11/1999 | Kutushov |
| 6,090,292 A | 7/2000 | Zimmermann et al. |
| 6,193,681 B1 | 2/2001 | Davidner et al. |

FOREIGN PATENT DOCUMENTS

| DE | 41 13 602 | 10/1992 |
| DE | 195 49 420 | 9/1997 |
| EP | 0 424 698 | 5/1991 |
| GB | 2192633 | 1/1988 |
| WO | WO 01/23413 | 4/2001 |

OTHER PUBLICATIONS

Abraham, et al., "Efficacy and Safety of Monoclonal Antibody to Human Tumor Necrosis Factor $\alpha$ in Patients With Sepsis Syndrome", JAMA, Mar. 22/29, 1995, pp. 934–941, vol. 273, No. 12.
Bernard, et al., "The Effects of Ibuprofen on the Physiology and Survival of Patients with Sepsis", The New England Journal of Medicine, Mar. 27, 1997, pp. 912–918, vol. 336, No. 13.
Bernard, et al., "Efficacy and Safety of Recombinant Human Activated Protein C for Severe Sepsis", The New England Journal of Medicine, Mar. 8, 2001, pp. 699–709, vol. 344, No. 10.
Bernard, et al., "Prostacyclin and Thromboxane $A_2$ Formation Is Increased in Human Sepsis Syndrome", American Review of Respiratory Disease, Nov. 1991, pp. 1095–1101, vol. 144, No. 5.

Bone, et al., "Sepsis syndrome: A valid clinical entity", Critical Care Medicine, May 1989, pp. 389–393, vol. 17, No. 5.
Cohen, et al., "INTERSEPT: An international, multicenter, placebo–controlled trial of monoclonal antibody to human tumor necrosis factor–$\alpha$ in patients with sepsis", Critical Care Medicine, Sep. 1996, pp. 1431–1440, vol. 24, No. 9.
Dhainaut, et al., "Platelet–activating factor receptor antagonist BN 52021 in the treatment of severe sepsis: A randomized, double–blind, placebo–controlled, multicenter clinical trial", Nov. 1994, pp. 1720–1728, vol. 22, No. 11.
Dhainaut, et al., "CDP571, a humanized antibody to human tumor necrosis factor–$\alpha$: Safety, pharmacokinetics, immune response, and influence of the antibody on cytokine concentrations in patients with septic shock", Sep. 1995, pp. 1461–1469, vol. 23, No. 9.
Duff et al., "Removal of Endotoxin By a Polymyxin B Affinity Column", Clinical Research, Apr. 1982, p. 565A, vol. 30, No. 2.
Fein, et al., "Treatment of Severe Systemic Inflammatory Response Syndrome and Sepsis with a Novel Bradykinin Antagonist, Deltibant (CP–0127)", Feb. 12, 1997, JAMA, vol. 277, No. 6.
Fisher, et al., "Initial evaluation of human recombinant interleukin–1 receptor antagonist in the treatment of sepsis syndrome: A randomized, open–label, placebo–controlled multicenter trial", Critical Care Medicine, Jan. 1994, pp. 12–21, vol. 22, No. 1.
Fisher, et al., "Recombinant Human Interleukin 1 Receptor Antagonist in the Treatment of Patients With Sepsis Syndrome", JAMA, Jun. 15, 1994, pp. 1836–1843, vol. 271, No. 23.

(List continued on next page.)

*Primary Examiner*—Sandra E. Saucier
(74) *Attorney, Agent, or Firm*—Catalyst Law Group, APC; Michael B. Farber, Esq.

(57) ABSTRACT

In general, a method for removal of pyrogens from plasma or blood according to the present invention comprises: (1) passing the biological fluid through a resin comprising two components: (a) a first component comprising a polymeric support with a multiplicity of ligands comprising a $C_{10}$–$C_{24}$ alkylamino group, the ligands specifically binding endotoxin; and (b) a second component comprising a halogenated quinolone moiety immobilized on an amino-group-containing solid support by the formation of an amide linkage, the first component and the second component being present in the resin at a ratio of from about 20:80 (v/v) to about 80:20 (v/v); and (2) collecting the biological fluid from which pyrogens have been removed. Preferably, the alkylamino group is a stearylamino group, and the ligands are cross-linked and quaternized by reaction with a dibromoalkanol. Preferably, the polymeric support of the first component is agarose in particulate form. Preferably, the halogenated quinolone moiety is ($\pm$)-9-fluoro-2,3-dihydro-3-methyl-10-(4-methyl-1-piperazinyl)-7-oxo-7H-pyrido[1,2,3-de]-1,4-benzoxazine-6-carboxylic acid. The invention also includes resins useful in methods according to the present invention and cartridges incorporating such resins.

62 Claims, 4 Drawing Sheets

OTHER PUBLICATIONS

Fisher Jr., et al., "Influence of an anti–tumor necrosis factor monoclonal antibody on cytokine levels in patients with sepsis", Critical Care Medicine, Mar. 1993, pp. 318–327, vol. 21, No. 3.

Fisher Jr, et al., "Treatment of Septic Shock with the Tumor Necrosis Factor Receptor: Fc Fusion Protein", The New England Journal of Medicine, Jun. 27, 1996, pp. 1697–1702, vol. 334, No. 26.

Haupt, et al., "Effect of ibuprofen in patients with severe sepsis: A randomized, double–blind, multicenter study", Critical Care Medicine, Nov. 1991, pp. 1339–1347, vol. 19, No. 11.

Kluger, et al., "Polymyxin B Use Does Not Ensure Endotoxin–Free Solution", Journal of Immunological Methods, 1985, pp. 201–207.

Kodama, et al., "Hemoperfusion using a polymyxin B immobilized fiber column for the removal of endotoxin", Endotoxin Research Series, 1993, pp. 389–398, vol. 2.

Kox, et al., "Immunomodulatory therapies in sepsis", Intensive Care Medicine, 2000, pp. S124–S128, vol. 26, Supp. 1.

Marshall, et al., "Multiple Organ Dysfunction Score: A reliable descriptor of a complex clinical outcome", Critical Care Medicine, Oct. 1995, pp. 1638–1652, vol. 23, No. 10.

Miyashima, et al., "Initiation and Recovery Processes of Endotoxin Induced Disseminated Intravascular Coagulation (DIC): Scanning and Transmission Electron Microscopic Observations of Rat Renal Tissues", Acta Medica Okayama, Apr. 1989, vol. 43, No. 2.

Opal, et al., "Confirmatory interleukin–1 receptor antagonist trial in severe sepsis: A phase III, randomized, double–blind, placebo–controlled, multicenter trial," Critical Care Medicine, Jul. 1997, pp. 1115–1124, vol. 25, No. 7.

Reinhart, et al., "Assessment of the safety and efficacy of the monoclonal anti–tumor necrosis factor antibody–fragment, MAK 195F, in patients with sepsis and septic shock; A multicenter, randomized, placebo–controlled, dose–ranging study", Critical Care Medicine, May 1996, pp. 733–742, vol. 24, No. 5.

Sieradzki, et al., "The Development of Vancomycin Resistance in A Patient with Methicillin–Resistant *Staphylococcus aureus* Infection", The New England Journal of Medicine, Feb. 18, 1999, pp. 517–523, vol. 340, No. 7.

Smith, et al., "Emergence of Vancomycin Resistance in *Staphylococcus aureus*", The New England Journal of Medicine, Feb. 18, 1999, pp. 493–501, vol. 340, No. 7.

Taylor Jr., "Protein C Prevents the Coagulopathic and Lethal Effects of *Escherichia coli* Infusion in the Baboon", The Journal of Clinical Investigation, Mar. 1987, pp. 918–925, vol. 79, No. 3.

Tracey, et al., "Tumor necrosis factor: An updated review of its biology", Critical Care Medicine, Oct. 1993, pp. S415–S421, vol. 21, No. 10.

METHOD FOR REMOVING PYROGENS FROM PLASMA AND BLOOD FOR TREATMENT OF SEPTIC SHOCK

BACKGROUND OF THE INVENTION

General Background and State of the Art

This invention is directed to methods for pyrogen removal from plasma and whole blood.

The presence of pyrogens in the blood is responsible for inflammatory reactions that, if they go unchecked, can be fatal, such as in the case of septic shock. Currently, the leading cause of death in intensive care units (ICUs) is multiple organ failure (MOF). The mortality of patients in ICUs due to septic shock is about 30%. There are approximately 500,000 patients per year suffering from sepsis in the U.S., and the number of deaths related to sepsis syndrome is increasing every year (200,000 deaths/year) as well as the death rate. Decades of research to overcome septicemia or even decrease the mortality rate have been unsuccessful and disheartening.

The concept of MOF was developed in 1975. In the etiology of MOF, the frequency of infection, sepsis, and inflammation is very high. The original classification of Bone (Bone, Crit Care Med 1989, 7:389–393), identifying sepsis and septic shock was later revised (Members of the American College of Chest Physicians 1992), and a new terminology was developed. The definition of systemic inflammatory response syndrome and the multiple organ dysfunction syndrome (MODS) were worked out. Sepsis, severe sepsis and septic shock were also redefined. The Marshall score (Marshall, Crit Care Med 1995, 23:1638–1652) has been accepted to describe the severity of MODS.

The pathogenesis of sepsis begins with the proliferation of microorganisms at a nidus of infection followed by invasion of the bloodstream and other organs. Gram-negative bacteria account for a large fraction of cases of sepsis. The structural component of Gram-negative bacteria, endotoxin (ET) or lipopolysaccharide (LPS), plays a pivotal role in the initiation and development of the sepsis syndrome. The most widely accepted theory of sepsis is based on the following line of thought. ET binds to the CD14 receptor and leads to the activation of monocytes and other cells carrying this receptor. The binding results in transcriptional changes in the nucleus of activated cells, and the synthesis of different inflammatory compounds, such as Platelet Activating Factor-1, pro-inflammatory cytokines such as TNF-α, Interleukin-1 (IL-1) or IL-6 leading to a systemic inflammatory response.

The immunological pattern of sepsis has a biphasic manifestation. The early hyper-inflammatory phase is counterbalanced by an anti-inflammatory response (the release of soluble cytokines and cytokines receptors, e.g. IL-10, IL-1 Receptor antagonist and the synthesis of anti-cytokine antibodies). The induction of imbalanced production of different cytokines is part of the pathology of septic shock. When the anti-inflammatory response is in measure with the hyper-inflammatory reactions, the clinical outcome is usually favorable. However, either the hyper-inflammatory or the anti-inflammatory mechanism may become uncontrolled, leading to serious organ damage, organ failure and death. In this frame of thinking, early mortality is related to excessive systemic inflammatory response, while late mortality is caused by immunodepression, in the late, so-called hypo-inflammatory state, also called the state of terminal immuno-paralysis (Kox, Int Care Med 2000, 26:S124–128).

In the vast majority of septic shock cases, disseminated intravascular coagulation (DIC) is also diagnosed, and that DIC often leads to different organ failures. The relationship between ET and DIC has been investigated. In animal models, ET is often used to induce DIC. It has been thought that in those cases, DIC is primarily initiated by injury to the capillary endothelium, and that changes on the endothelial surface contribute to the development of DIC (Miyashima, Acta Med Okayama 1989, 43(2): 115–126).

Gram-negative septicemia elicits multiple abnormalities of the coagulation system. Although products of coagulation can lead to clot formation, potentiating organ damage, it has also been shown that low concentrations of thrombin can protect animals from the shock state by leading to in vivo formation of activated Protein C, an anticoagulant enzyme. In baboons, when *E. coli* was used to induce sepsis, lethal responses were prevented by infusion of exogenous Protein C (Taylor, J Clin Inves 1987, 79:918–925).

Because of the complexity of the pathology and the numerous factors involved, the treatment of sepsis has proved itself to be difficult, expensive and so far an unrewarding task.

With the emergence of antibiotic-resistant infections, the treatment of sepsis has become even more difficult. A number of microorganisms are of great concern in terms of their resistance. For example, Methicillin-Resistant *Staphylococcus aureus* has become an important cause of infection, not only in the ICUs of hospitals, but in the community as well. Strains of Vancomycin-Intermediate *S. aureus* have also recently been identified (Sieradzki, N Engl J Med 1999, 340:517–523; Smith, N Engl J Med 1999, 340:493–501). They are difficult to detect with standard laboratory methods, which increases the risk they represent. Vancomycin-Resistant Enterococci infections have increased 47% among ICU patients in the last five years.

The great majority of therapeutic modalities for sepsis of the last decade, include treatments with antibodies, soluble receptors and recombinant protein constructs to block the effect of one or another mediator contributing to the circulatory collapse, MOF and death of sepsis patients. They were based on the concept of sepsis characterized by changes in pro-inflammatory mediators, cytokines, growth factors and lipid metabolites. Synergen initiated three trials with Antril (IL-1 receptor antagonist). The drug had no significant effect in septic patients (Opal, Crit Care Med 1997, 25(7): 1115–1124; Fisher, Crit Care Med 1994, 22(1):12–21 and JAMA 1994, 271(23):1836–1843). Platelet activating factor antagonist (Dhainaut, Crit Care Med 1994, 22(11): 1720–1728 and 1995, 23(9):1461–1469), bradykinin antagonists [Rodell, Press release Cortech Inc, Jul. 18, 1995; Fein, JAMA 1997, 277(6):482–487), anti-TNF antibodies [Reinhart, Crit Care Med 1996, 24:733–792; Fisher, Grit Care Med 1993, 21(3):318–327; Dhainaut, Crit Care Med 1995, 23(9):1461–1469; Abraham, JAMA 1995, 273(12):934–941; Cohen, Crit Care Med 1996, 24 (9):1431–1440), soluble TNF receptors (Fisher, N Engl J Med 1996, 334(26):1697–1702; Abraham, JAMA 1995, 273(12):934–941) and prostaglandin antagonists (Bernard, N Engl J Med 1997,336(13):912–918; Haupt, Crit Care Med 1991, 19(11):1339–1347; Bernard, Am Rev Respir Dis 1991,144(5):1095–1101) were also tried in recent clinical investigations. None of these clinical trials succeeded in identifying an effective new treatment modality for septic shock.

There are current trials still in process. Most recently, results of a phase 3 clinical trial were reported (Bernard, N Engl J Med 2001, 344(10): 699–709). Dotrecogin α-activated (24 μg/kg i.v.) was used in that multi-center trial, and a 6.1% reduction in the absolute risk of death was achieved.

For now, the standard treatments of septic shock continue to be urgent stabilization of the patient, volume resuscitation, vasopressors and/or inotropic therapy to restore perfusion, and the administration of broad spectrum, empirical antibiotic therapy in the setting of an ICU. Monitoring strategies and adjunctive therapy are also useful.

High ET levels are consistently measured in the blood of patients with severe septic shock syndrome. In many cases, the clinical picture correlates with the level of LPS in the blood of the patients. Removal of ET from their blood remains to be ultimately desirable. The LPS theory has been extensively explored, and results show that once the cascade of LPS, CD14, pro-inflammatory proteins and cytokines has been set in motion, further active downstream substances are produced, and they contribute to the often irreversible pathophysiology of the disease. With regard to the administration of LPS antibodies, the therapy failure is due partly to a too low specificity or affinity between the very heterogeneous LPS molecules and the monoclonal or polyclonal antibodies used.

Our novel technology, unlike most previous approaches, is not based on the inactivation principle or the supplementation of biologically active molecules, but rather on the removal of ET. The present invention offers great novelty in that it is an affinity-based technology and it removes the causative agents of sepsis directly from the patient's blood.

Extracorporeal strategies such as continuous renal replacement therapy or therapeutic plasmapheresis in uncontrolled sepsis trials have shown benefit. However, these methods are limited because of their lack of specificity of removal of pathognomic and toxic substances from the blood. The need for specific removal of substances implicated in septic shock has been well recognized and advocated by experts in the field. The removal of ET and pyrogens from plasma and/or whole blood in an extracorporeal setting could improve the outcome of this serious illness. In sepsis, the early removal of ET would be most beneficial, but it remains to be beneficial in the later clinical stages as well. Other than the very early phase of septic syndrome, when removal of ET may make a difference in terms of survival, there is the late stage of the immunoparalysis, in which the patients are defenseless against new infections and respond less to new triggering factors due to the exhaustion of their immune system (severe burn, trauma cases, etc.).

General methods and systems to remove specific toxins from a biological fluid such as plasma or blood have been reported. For instance, Kutushov (U.S. Pat. No. 5,980,479) proposes the use of magneto-conductive particles to which an antibody to a specific toxin has been bound, for the removal of the toxin from a biological fluid. The particles are directly mixed with the fluid and flow through an extracorporeal flow line and then are retained in a magnetic field region.

U.S. Pat. No. 6,090,292 discloses a device where albumin coated acrylic beads are the base material for removing albumin bound proteins, such as mercaptans, free fatty acids, unconjugated bilirubin and ET. Nonspecificity is a characteristic of this technology. In addition, ET removal demonstrated for this device is not relevant to levels found in septic patients: 76% of 10,000 EU/ml were removed, which leaves 2,400 EU/ml ET in the blood. This is far too high a level of residual ET to provide effective treatment.

Other patents describe various methods of non-specific removal of toxic mediators of sepsis inflammatory response syndrome usually composed of many filters and units (U.S. Pat. No. 5,571,415; U.S. Pat. No. 6,193,681). German Patent No. DE 19938394 uses ET-specific antibodies that are often difficult and costly to produce. The use of natural and synthetic cationic peptides has also been suggested (U.S. Pat. No. 6,337,317), but only limited amounts can be isolated from the host species, and peptide technology is expensive when scaled up to large volumes.

The validity of lowering plasma ET levels in the treatment of septic shock has been supported by others (Duff, Clin Res 1982, 30:565A; Kodama, Elsevier Science Publishers, J Levin, C R Alving, R S Mundorf, P L Stutz eds 1993, 389–398). A promising hemoperfusion method, using polymyxin B (PMX) immobilized onto polystyrene fibers for the removal of ET was shown to reduce plasma levels of ET in septic patients, and it was evaluated in a multicenter clihical study. 52% of 42 patients survived at day 14 after PMX treatment (Kodama, Elsevier Science Publishers 1993). However, it has also been shown (Kluger, J Immunol Methods 1985, 83:201–207) that PMX removes some, but not all ET from solutions. Porous support materials with immobilized PMX have been disclosed in U.S. Pat. No. 4,576,928; DE Patent No. 3,932,971 and GB Patent No. 2192633. However, the clinical application of this affinity support is very problematic since the ligand PMX causes severe nephrotoxic and neurotoxic damage when released into the blood circulation. Accordingly, the use of PMX has limited value.

The polyethylenimine modified cellulose material disclosed in DE Patent No. 4113602 has low binding capacity for LPS, and the volume of extracorporeal blood would exceed the medically tolerable limit.

Polyanion-modified support material described in U.S. Pat. No. 5,403,917 and DE Patent No. 4331358 for the extracorporeal adsorption of TNF-α and LPS from whole blood and/or plasma is not selective. In addition, cation exchangers have moderate affinity for negatively charged LPS at physiological pH. Only 30% of LPS can be removed by this method. Again, this is not sufficient removal for efficient treatment of septic shock.

In U.S. Pat. No. 5,679,775 and DE Patent No. 19549420, a cation exchanger and an anion exchanger material are used as an extracorporeal perfusion system. However, ET level in treated plasma remains high (4.1 EU/ml), and is far above the safe limit. An identical observation can be made with respect to WO Patent Publication No. WO 01/23413, which in addition, uses oligopeptides, which are expensive to synthesize.

INVENTION SUMMARY

One aspect of the present invention is a method for removing pyrogens from a biological fluid selected from the group consisting of plasma and blood comprising the steps of:

(1) passing the biological fluid through a resin comprising two components: (a) a first component comprising a polymeric support with a multiplicity of ligands comprising a $C_{10}$–$C_{24}$ alkylamino group, the ligands specifically binding endotoxin; and (b) a second component comprising a halogenated quinolone moiety immobilized on an amino-group-containing solid support by the formation of an amide linkage, the first component and the second component being present in the resin at a ratio of from about 20:80 (v/v) to about 80:20 (v/v); and (2) collecting the biological fluid from which pyrogens have been removed.

Typically, the alkylamino group is a stearylamino group.

Typically, the polymeric support of the first component is agarose.

Typically, at least a proportion of the ligands of the first component are cross-linked. Preferably, the cross-linking is at the amino moiety of the alkylamino group, such as the stearylamino group. Preferably, the ligands are cross-linked by quaternization with an alkyl group, such as by reaction with a dibromoalkanol. A particularly preferred dibromoalkanol is 2,3-dibromopropanol.

Typically, the polymeric support of the first component is in particle form. Typically, the particles are from about 20 microns to about 900 microns in diameter. Preferably, the particles are from about 60 microns to about 300 microns in diameter. More preferably, the particles are from about 60 microns to about 100 microns in diameter.

Typically, the halogenated quinolone moiety of the second component is of formula (I) wherein $R_1$ is lower alkyl, $R_2$ is lower alkyl, and X is a halogen selected from the group consisting of fluoro, chloro, bromo, and iodo. Preferably, $R_1$ is methyl, R2 is methyl, X is fluoro, and the halogenated quinolone moiety is (±)9-fluoro-2,3-dihydro-3-methyl-10-(4-methyl-1-piperazinyl)-7-oxo-7H-pyrido[1,2,3-de]-1,4-benzoxazine-6-carboxylic acid, known as Floxin.

(I)

Typically, the amino-derivatized support of the second component is amino-derivatized agarose.

Typically, the halogenated quinolone moiety is immobilized to the amino-containing solid support by reaction with a carbodiimide. Preferred carbodiimides include, but are not limited to, 1-ethyl-3-(3-dimethylaminopropyl)carbodiimide, 1-cyclohexyl-3-(2-morpholinoethyl)carbodiimide, and N,N'-dicyclohexylcarbodiimide. A particularly preferred carbodiimide is 1-ethyl-3-(3-dimethylaminopropyl) carbodiimide.

Typically, the first component and the second component are present in a ratio of from about 60:40 (v/v) to about 40:60 (v/v). Preferably, the first component and the second component are present in a ratio of about 50:50 (v/v).

Preferably, the method removes pyrogens below the level of 0.25 EU/ml. Preferably, the method removes endotoxin.

Another aspect of the present invention is a resin comprising two components: (1) a first component comprising a polymeric support with a multiplicity of ligands comprising a $C_{10}$–$C_{24}$ alkylamino group, the ligands specifically binding endotoxin; and (2) a second component comprising a halogenated quinolone moiety immobilized on an amino-group-containing solid support by the formation of an amide linkage, the first component and the second component being present in the resin at a ratio of from about 20:80 (v/v) to about 80:20 (v/v). Particularly preferred resins are those described above in terms of the method.

Yet another aspect of the present invention is a cartridge for removal of pyrogens comprising:

(1) a housing for holding a resin, the housing having first and second ends;

(2) a resin according to the present invention as described above;

(3) an inlet attached to the first end of the housing for allowing a biological fluid selected from the group consisting of blood and plasma to flow into the housing; and (4) an outlet attached to the second end of the housing for allowing the biological fluid from which pyrogens have been removed to flow out of the housing.

BRIEF DESCRIPTION OF THE DRAWINGS

The following invention will become better understood with reference to the specification, appended claims, and accompanying drawings, where:

DETAILED DESCRIPTION OF THE PREFERRED EMBODIMENTS

One aspect of the present invention is a method for removing pyrogens from a biological fluid selected from the group consisting of blood and plasma. The method comprises the steps of:

(1) passing the biological fluid through a resin comprising two components: (1) a first component comprising a polymeric support with a multiplicity of ligands comprising a $C_{10}$–$C_{24}$ alkylamino group, the ligands specifically binding endotoxin; and (2) a second component comprising a halogenated quinolone moiety immobilized on an amino-group-containing solid support by the formation of an amide linkage, the first component and the second component being present in the resin at a ratio of from about 20:80 (v/v) to about 80:20 (v/v); and (2) collecting the biological fluid from which pyrogens have been removed.

Typically, the alkylamino group is a stearylamino group.

Typically, the polymeric support of the first component is agarose.

Typically, at least a proportion of the ligands of the first component are cross-linked. Preferably, the cross-linking is at the amino moiety of the alkylamino group, such as the stearylamino group. Preferably, the ligands are cross-linked by quaternization with an alkyl group, such as by reaction with a dibromoalkanol. A particularly preferred dibromoalkanol is 2,3-dibromopropanol.

Typically, the polymeric support of the first component is in particle form. Typically, the particles are from about 20 microns to about 900 microns in diameter. Preferably, the particles are from about 60 microns to about 300 microns in diameter. More preferably, the particles are from about 60 microns to about 100 microns in diameter.

Typically, the halogenated quinolone moiety of the second component is of formula (I) wherein $R_1$ is lower alkyl, $R_2$ is lower alkyl, and X is a halogen selected from the group consisting of fluoro, chloro, bromo, and iodo. As used herein, the term "lower alkyl" refers to an unbranched or branched alkyl group of from 1 to 6 carbon atoms; typically, "lower alkyl" refers to an unbranched alkyl group of from 1 to 6 carbon atoms. Preferably, $R_1$ is methyl, $R_2$ is methyl, X is fluoro, and the halogenated quinolone moiety is (±)-9-fluoro-2,3-dihydro-3-methyl-10-(4-methyl-1-piperazinyl)-7-oxo-7H-pyrido[1,2,3-de]-1,4-benzoxazine-6-carboxylic acid, known as Floxin.

(I)

Typically, the amino-derivatized support of the second component is amino-derivatized agarose.

Typically, the halogenated quinolone moiety is immobilized to the amino-containing solid support by reaction with a carbodiimide. Preferred carbodiimides include, but are not limited to, 1-ethyl-3-(3-dimethylaminopropyl)carbodiimide, 1-cyclohexyl-3-(2-morpholinoethyl)carbodiimide, and N,N'-dicyclohexylcarbodiimide. A particularly preferred carbodiimide is 1-ethyl-3-(3-dimethylaminopropyl) carbodiimide.

Typically, the first component and the second component are present in a ratio of from about 60:40 (v/v) to about 40:60 (v/v). Preferably, the first component and the second component are present in a ratio of about 50:50 (v/v).

Preferably, the method removes pyrogens below the level of 0.25 EU/ml. Preferably, the method removes endotoxin.

The technology of the present invention utilizes a patented proprietary large particle based support (U.S. Pat. No. 5,466,377, incorporated herein by this reference) that has high binding capacity and allows the free passage of cells between the particles, without requiring any fluidization. The immobilization chemistry has been extensively characterized for leaching and has been found to be stable. When the support is in the form of particles, the particles are preferably in the size range of 60–160 μm beads for ET adsorption from plasma and 200–300 μm range beads for ET adsorption from whole blood.

One of the resins used in this new method is Acticlean Etox™ (Sterogene Bioseparations, Inc., Carlsbad, Calif., USA) and it is extensively used as a solid phase reagent in bioprocesses (Smith and Grandics, Am Biotech Lab 2000, 18:39–40). It effectively removes ET from several biological media including DNA, proteins and bovine serum. Affinity of the immobilized ligand for proteins is very low, delivering a mass yield of proteins that exceeds 95%. The ET binding capacity of Acticlean Etox has been measured in buffers and protein solutions (up to 500,000 EU/ml). Acticlean Etox has favorable features such as it dissociating ET-protein complexes. This ligand is stable and non-toxic. This resin is further described in U.S. Pat. No. 6,106,723 by Grandics et al., incorporated herein in its entirety by this reference. In general, the resin is prepared by a process of: derivatizing a polymeric support with an epihalohydrin; reacting the derivatized support with a ($C_{10}$–$C_{24}$) alkylamine; and crosslinking at least a portion of the alkylamino groups and quaternizing at least a portion of the amino moieties by reacting the support with a halogenated alkyl alcohol. Preferably, the epihalohydrin is epibromohydrin.

The final resin of the invention is a mixture of Acticlean Etox and Floxin immobilized resins, preferably in equal amounts (50/50; v/v). The chemistry for Floxin immobilization is described in Example 1.

We have used a supernatant of *Pseudomonas maltophilia*, a Gram⁻ bacteria, as a model to spike plasma or whole blood and challenge the adsorbent.

The plasma or whole blood was pumped through the column at a flow rate of 0.6 ml/min. Samples were collected using sterile needle and syringes via a sample port.

To determine ET content in plasma samples and blood samples, the Limulus amoebocyte lysate (LAL) assay was used directly on heparinized plasma, or serum prepared from heparinized whole blood that clotted in the glass ET-free tubes used for collection. The use of citrated plasma or blood was prevented by the interference of citrate with the LAL assay.

Figure 1:
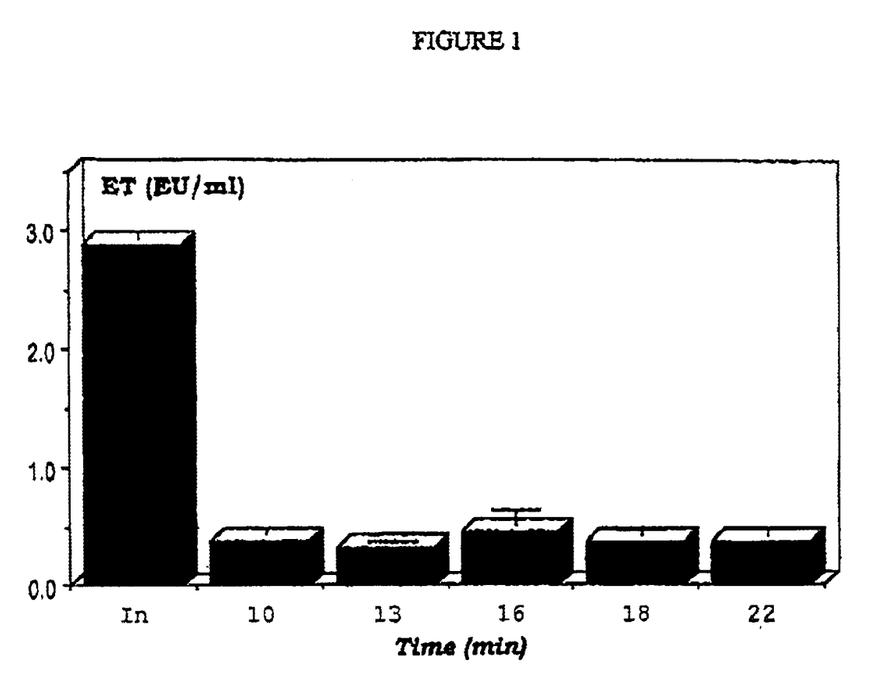
FIG. 1 is a graph showing that three cartridges according to the present invention placed in series result in depletion of endotoxin (ET) from 2 EU/ml (200 pg/ml) found in plasma of sepsis patients to <0.25 EU/ml.
Figure 2:
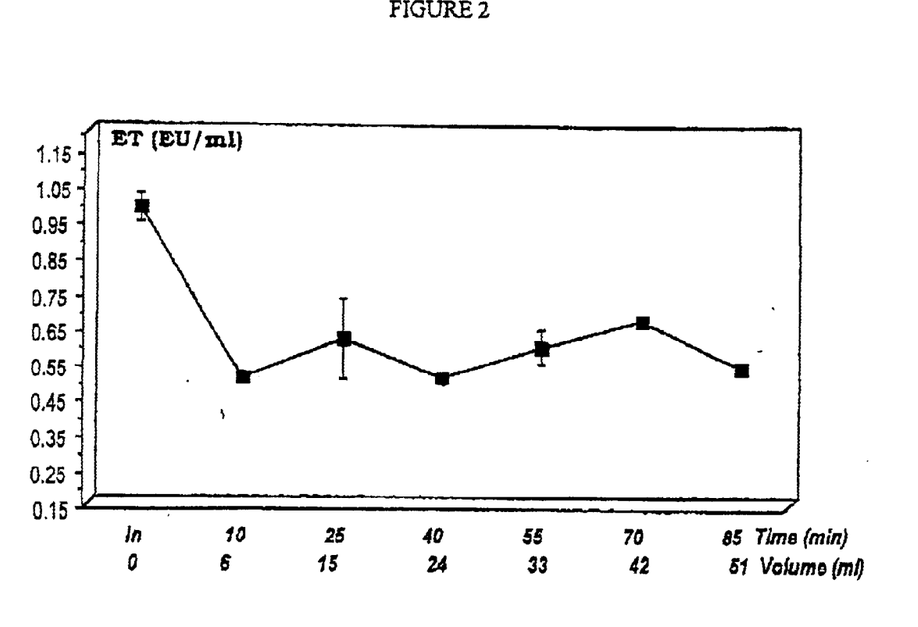
FIG. 2 is a graph showing that a volume of plasma up to 34 column volumes can be treated and that 50% of the loaded ET can be removed by one cartridge.

The new resin of the present invention is able to remove at least 50% of the loaded ET from plasma. Three cartridges of 1.5 ml placed in series result in ET depletion from 2 EU/ml (200 pg/ml) level found in plasma of sepsis patients, to <0.25 EU/ml (FIG. 1). A volume of plasma of up to 34 column volumes can be treated and 50% of the loaded ET can consistently be removed by one cartridge (FIG. 2).

We have found that the Floxin/Acticlean Etox resin can also remove ET from whole blood. When blood was spiked with 2.6 EU/ml ET, after passing through 1.5 ml of adsorbent (FIG. 4), post-column levels were between 0.4 and 1.6 EU/ml. For a spike of 0.75 EU/ml, the levels were brought down to <0.33 EU/ml.

Since non-LPS (LAL-negative) pyrogens also contribute to sample pyrogenicity, an assay other than the LAL test was used to evaluate pyrogens in samples. Such a test can be the USP rabbit pyrogenicity test. This is however rather tedious and impractical for this purpose for a variety of reasons. Moreover, the rabbit test does not provide information on sub-toxic, low level inflammatory reactions induced by the sample. A more suitable test is based upon the monocyte activation/cytokine assay that is the equivalent to the rabbit test in assessing total sample pyrogenicity. Monocytes, when exposed to pyrogenic substances, secrete inflammatory cytokines (IL-1, IL-6, IL-8, TNF-α, etc.) that can be detected at very low levels. Induction of TNF-α secretion by monocytes was used as an in vitro assay system for pyrogen-induced inflammatory reactions. TNF-α is an important early mediator of host responses to ET contamination, and is induced in vitro by ET challenge. TNF-α can also induce the production of IL-1 in various cell types, as well as IL-6 (Shalaby, Clin Immunol Immunopathol 1989, 53(3): 488–498). TNF-α is the only endogenous mediator capable of triggering the entire spectrum of metabolic, hemodynamic, tissue and cytokine cascade responses of septic shock (Tracey, Crit Care Med 1993, 21 (10 Suppl): S415–422). We have found that the Floxin/Acticlean Etox resin greatly reduced TNF-α production.

Figure 3:
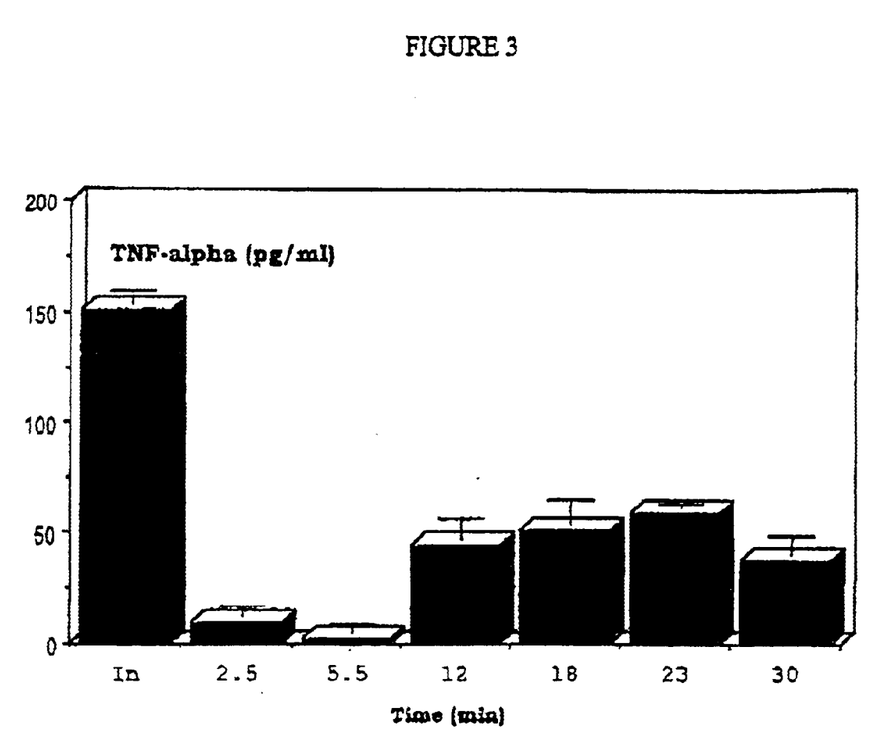
FIG. 3 is a graph showing that TNF-α secretion was significantly decreased by 29.4% to 98.4% in samples post- as compared with pre-adsorption resin.

The details of these experiments are described under Examples and in FIG. 3.

In order to assess the efficiency of removal of infectious agents, *Pseudomonas maltophilia* was used as a model of Gram⁻ bacteria. Floxin/Acticlean Etox (1.5 ml) was able to remove between 20 and 60% of bacteria from plasma (Example 11).

Another aspect of the present invention is a resin comprising two components: (1) a first component comprising a polymeric support with a multiplicity of ligands comprising a $C_{10}$–$C_{24}$ alkylamino group, the ligands specifically binding endotoxin; and (2) a second component comprising a halogenated quinolone moiety immobilized on an amino-group-containing solid support by the formation of an amide linkage, the first component and the second component being present in the resin at a ratio of from about 20:80 (v/v) to about 80:20 (v/v). Particularly preferred resins are those described above in terms of the method.

Yet another aspect of the present invention is a cartridge for removal of pyrogens comprising:

(1) a housing for holding a resin, the housing having first and second ends;
(2) a resin according to the present invention as described above;
(3) an inlet attached to the first end of the housing for allowing a biological fluid selected from the group consisting of blood and plasma to flow into the housing; and
(4) an outlet attached to the second end of the housing for allowing the biological fluid from which pyrogens have been removed to flow out of the housing.

Preferred resins are those described above.

The cartridges can be coupled in series, so that two or more cartridges can be coupled together, the outlet of one cartridge being attached to the inlet of the next. Accordingly, another aspect of the present invention is an assembly comprising a plurality of cartridges according to the present invention connected in series so that the outlet of each cartridge is connected to the inlet of the next cartridge.

The invention is illustrated by the following Examples. These Examples are for illustrative purposes only and are not intended to limit the invention.

EXAMPLE 1

Preparation of Floxin resin: Floxin (Ofloxacin, Sigma) is immobilized on agarose amino gels using carbodiimides such as 1-ethyl-3-(3-dimethylaminopropyl) carbodiimide (EDC), which has been widely used in conjugation reactions, peptide synthesis, and as an immobilization reagent in the preparation of affinity gels. The reaction is typically performed at pH 4.5 with 10 mg of both Floxin and EDC per ml of resin, overnight at room temperature.

EXAMPLE 2

Preparation of *Pseudomonas maltophilia* culture supernatant: *Pseudomonas maltophilia* was obtained from ATCC#17666 Aug. 10, 1966, and the bacterial culture broth from Difco Laboratories (Detroit, Mich.) was used for culture. The culture was grown at 37° C., and LPS in the supernatant was monitored periodically by the LAL assay. The total culturing time was 48 hours. Then the culture was refrigerated at 4° C. and centrifuged at 2,000×g. To the supernatant, 20 μg/ml Gentamycin (Sigma, St Louis, Mo.) and 5 μg/ml Ciproflaxin (Bayer, West Haven, Conn.) were added. The supernatant was sterile filtered and aliquoted for freeze storage. The sterility of the filtrate was ascertained using agar-plate culture. No colony growth was observed. The LPS concentration was 80,000 EU/ml.

EXAMPLE 3

Preparation of the system for ET removal from plasma: Equal volumes of Floxin resin (60–160 μm beads) and Acticlean Etox resin (60–160 μm beads) were mixed to produce the resin designated Floxin/Acticlean Etox (60–160 μm). A glass column was packed with 1.5 ml of Floxin/Acticlean Etox resin. At 3 ml/min, 1 N sodium hydroxide (NaOH, 25 ml) was pumped into the column and was allowed to sit in the column overnight. The column and the tubing were rinsed to neutrality with ET-free LAL-water. A sample port was also decontaminated with 1 N NaOH overnight and rinsed under sterile conditions with LAL-water, before being placed at the outlet of the column.

EXAMPLE 4

Preparation of plasma: Plasma or serum was prepared from whole blood by spinning the blood at 1,800 g for 20 minutes at 12 degree C. Heparin (5–20 U/ml) was used as anticoagulant. The resulting supernatant was sterile filtered with a 0.22 μm cut-off filter.

EXAMPLE 5

ET adsorption from plasma: The column, prepared as described in Example 3, was perfused with heparinized plasma (heparin 5–20 EU/ml) spiked with ET amounts in the range found in septic shock patients (0.5–7 EU/ml), at a flow rate of 0.6 ml/min, and fractions were collected periodically using sterile needles and syringes via a sample port. ET was measured by the LAL assay. Consistently, ET was decreased by 39 to 84% as indicated in Table 1 in experiments 1 and 2. When 3 columns were placed consecutively, the level of ET was brought from 2 EU/ml down to <0.25 EU/ml. This last experiment is illustrated in FIG. 1.

TABLE 1

| ET ADSORPTION FROM PLASMA | | |
|---|---|---|
| Sample | EU/ml (Exp. 1) | EU/ml (Exp. 2) |
| Pre-column | 2.89 | 6.86 |
| Post- 5 min | 0.45 | nt |
| Post- 12 min | 0.49 | nt |
| Post- 18 min | nt | 2.17 |
| Post- 25 min | 1.26 | nt |
| Post- 27 min | nt | 3.03 |
| Post- 36 min | nt | 3.87 |
| Post- 42 min | 1.72 | 4.19 | nt: not tested

EXAMPLE 6

LAL assay: Plasma or serum were diluted at least 20 times to maintain >50% ET recovery (limit of the LAL assay method) and heat-inactivated at 75° C. for 15 minutes. The LAL assay-kit containing control standard ET and lysate, was purchased from Charles River (Charleston, S.C.) and used as per manufacturer's instructions.

EXAMPLE 7

Preparation of the system for ET removal from whole blood: Equal volumes of Floxin resin (200–300 μm beads) Acticlean Etox resin (200–300 μm beads) were mixed to produce the resin designated Floxin/Acticlean Etox (200–300 μm). A plastic column was used in order to avoid activation of the coagulation intrinsic pathway. The column was packed with 1.5 ml of Floxin/Acticlean Etox resin. At 3 ml/min, 1 N NaOH (25 ml) was pumped into the column and was allowed to sit in the column overnight. The column and the tubing were rinsed to neutrality with ET-free LAL-water. The resin was then primed at 3 ml/min with 15 ml ET-free saline solution (0.9% NaCl), prepared from 15% NaCl sterile solution (Sigma, St Louis, Mo.) and LAL-water.

EXAMPLE 8

Figure 4:
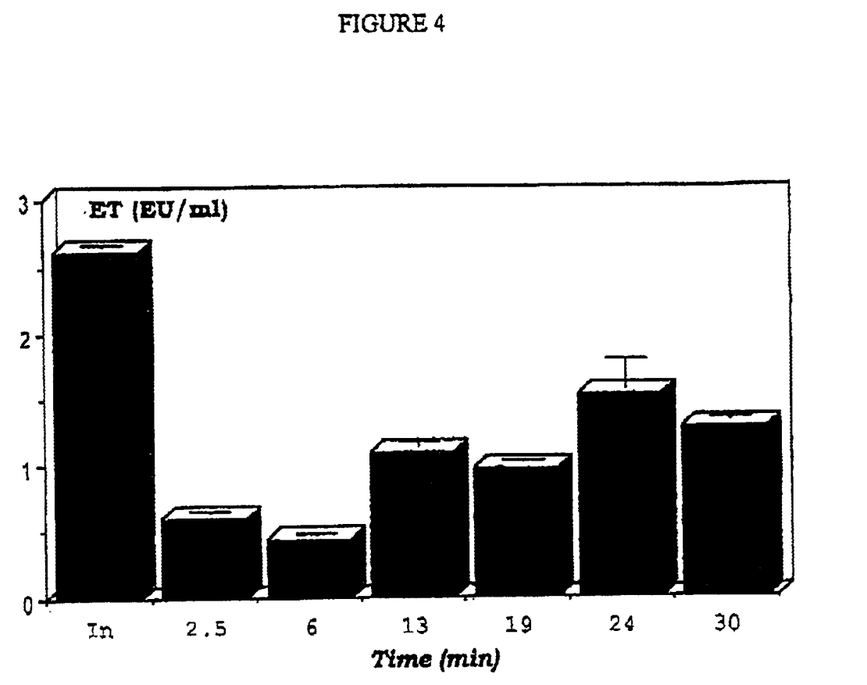
FIG. 4 is a graph showing that ET was effectively removed from whole blood, being decreased by 40% to 84% after whole blood was treated.

ET removal from whole blood: The column, prepared as described in Example 7, was perfused with heparinized blood (heparin 5 EU/ml) spiked with ET amounts in the range found in septic shock patients (0.5–7 EU/ml), at a flow rate of 0.6 ml/min, and fractions were collected periodically using sterile needles and syringes via a sample port. ET was measured by the LAL assay on serum obtained after centrifugation of whole blood fractions collected in endotoxin-free glass tubes. Consistently, ET was decreased by 40 to 84% as shown in FIG. 4.

EXAMPLE 9

Preparation of human monocytes and ET challenge: Monocytes were prepared by Ficoll separation of peripheral blood, and removal of non-adherent cells as follows. The mononuclear cells were incubated at a density of $10^6$ cells/well in 6-well plates, overnight in RPMI-1640 (containing 100 U/ml Penicillin/Streptomycin and 2 mM Glutamine) supplemented with 20% FCS. Adherent cells were then incubated in 0.75 ml RPMI-1640 (2×) containing 6% FCS+ 0.75 ml tested samples: citrated plasma from pre-adsorption resin spiked with 200 EU/ml (In), and various samples post-adsorption resin collected at various times.

Non-treated cells (supplemented with 0.75 ml unspiked-plasma) were used as baseline TNF-α production, which was subtracted from each sample value. TNF-α was measured from the culture supernatant after 24 hours incubation, using an ELISA-kit according to manufacturer's instructions (Cell Sciences, Norwood, Mass.).

TNF-α secretion by monocytes was significantly decreased by 29.4% to 98.4% in samples post-compared to pre-adsorption resin. These results therefore indicate that pyrogenic substances have been removed effectively.

EXAMPLE 10

Sandwich ELISA to quantify TNF-α: For this assay, the TNF-α ELISA kit from Cell Sciences (Norwood, Mass.) was used. The kit contains a 96-well microtiter plate with immobilized anti-TNF-α, TNF-α standards, antibody and peroxidase substrate. The absorbance was measured at 450 nm. The assay was performed following the manufacturer's directions.

EXAMPLE 11

Bacterial removal from plasma: *Pseudomonas maltophilia*, grown as in example 2, was diluted in sterile water to obtain approximately $10^7$ CFU/ml (estimated by the turbidity of the solution). This suspension was diluted at $10^4$, $10^2$ and 10 CFU/ml, and plated onto TSA agar plates to measure accurately the bacterial concentration. A solution of 287 CFU/ml of plasma was loaded onto Floxin/Acticlean Etox (60–160 μm), prepared as in Example 3, and ran through the column at 0.187 ml/min. Post-column samples were collected and the bacterial concentration was measured by plating bacteria on TSA agar plates. The adsorbent removed between 20 and 69% of bacteria present in the plasma. The results are shown in Table 2.

TABLE 2

BACTERIAL REMOVAL FROM PLASMA

| Sample | CFU/ml |
|---|---|
| Pre-column | 287 |
| Post-column 10 min | 90 |
| Post-column 23 min | 215 |
| Post-column 36 min | 163 |
| Post-column 50 min | 187 |
| Post-column 57 min | 229 |

ADVANTAGES OF THE INVENTION

The present invention provides a low-cost, efficient process for removing ET, pyrogens and bacteria from complex protein and cellular mixtures such as plasma and whole blood. This process can be particularly suitable for the treatment of septic shock. Although the present invention has been described in considerable detail, with reference to certain preferred versions thereof, other versions and embodiments are possible. It will be understood that in giving the preferred embodiment and application of the invention, the concept and scope of the invention is not limited to the specific reagents but certain changes and modifications may be practical within the scope of the appended claims. Therefore, the scope of the invention is determined by the following claims, and it is intended that the protection be limited only by the definitions of the appended claims.

What is claimed is:

1. A method for removing pyrogens from a biological fluid selected from the group consisting of plasma and blood comprising the steps of:
   (a) passing the biological fluid through a resin comprising two components: (1) a first component comprising a polymeric support with a multiplicity of ligands comprising a $C_{10}$–$C_{24}$ alkylamino group, the ligands specifically binding endotoxin; and (2) a second component comprising a halogenated quinolone moiety immobilized on an amino-group-containing solid support by the formation of an amide linkage, the first component and the second component being present in the resin at a ratio of from about 20:80 (v/v) to about 80:20 (v/v); and
   (b) collecting the biological fluid from which pyrogens have been removed.

2. The method of claim 1 wherein the alkylamino group of the first component is a stearylamino group.

3. The method of claim 1 wherein the polymeric support of the first component is agarose.

4. The method of claim 1 wherein at least a portion of the ligands of the first component are cross-linked.

5. The method of claim 4 wherein cross-linking is at the amino moiety of the alkylamino group.

6. The method of claim 5 wherein the ligands are cross-linked by quaternization with an alkyl group.

7. The method of claim 6 wherein the ligands are cross-linked by reaction with a dibromoalkanol.

8. The method of claim 7 wherein the dibromoalkanol is 2,3-dibromopropanol.

9. The method of claim 1 wherein the polymeric support of the first component is in particle form.

10. The method of claim 9 wherein the particles are from about 20 microns to about 900 microns in diameter.

11. The method of claim 10 wherein the particles are from about 60 microns to about 300 microns in diameter.

12. The method of claim 11 wherein the particles are from about 60 microns to about 100 microns in diameter.

13. The method of claim 1 wherein the first component comprises an agarose support in particle form of between about 60 microns to about 100 microns in diameter.

14. The method of claim 1 wherein the polymeric support of the first component is agarose in particle form with a diameter of between about 60 microns to about 100 microns in diameter and the alkylamino group of the first component is a stearylamino group that is cross-linked at at least a portion of the amino moieties of the stearylamino group by reaction with 2,3-dibromopropanol.

15. The method of claim 1 wherein the halogenated quinolone moiety is of formula (I) wherein $R_1$ is lower alkyl, $R_2$ is lower alkyl, (I)

and X is a halogen selected from the group consisting of fluoro, chloro, bromol and iodo.

16. The method of claim 15 wherein $R_1$ is methyl, $R_2$ is methyl, X is fluoro, and the halogenated quinolone moiety is (±)9-fluoro-2,3-dihydro-3-methyl-10-(4-methyl-1-piperazinyl)-7-oxo-7H-pyrido[1,2,3-de]1,4-benzoxazine-6-carboxylic acid.

17. The method of claim 15 wherein the amino-containing solid support is amino-derivatized agarose.

18. The method of claim 15 wherein the halogenated quinolone moiety is immobilized to the amino-containing solid support by reaction with a carbodiimide.

19. The method of claim 18 wherein the carbodiimide is selected from the group consisting of 1-ethyl-3-(3-dimethylaminopropyl)carbodiimide, 1-cyclohexyl-3-(2-morpholinoethyl)carbodiimide, and N,N'-dicyclohexylcarbodiimide.

20. The method of claim 19 wherein the carbodiimide is 1-ethyl-3-(3-dimethylaminopropyl) carbodiimide.

21. The method of claim 1 wherein the first component and the second component are present in a ratio of from about 60:40 (v/v) to about 40:60 (v/v).

22. The method of claim 21 wherein the first component and the second component are present in a ratio of about 50:50 (v/v).

23. The method of claim 1 wherein the biological fluid is blood.

24. The method of claim 1 wherein the biological fluid is plasma.

25. The method of claim 1 wherein the method removes pyrogens below the level of 0.25 EU/ml.

26. The method of claim 1 wherein the method removes endotoxin.

27. A method for removing pyrogens from a biological fluid selected from the group consisting of plasma and blood comprising the steps of:

(a) passing the biological fluid through a resin comprising two components: (1) a first component comprising a particulate agarose support with a particle diameter of from about 60 microns to about 100 microns with a multiplicity of ligands comprising a stearylamino group cross-linked by reaction with 2,3-dibromopropanol, the ligands specifically binding endotoxin; and (2) a second component comprising (±)9-fluoro-2,3-dihydro-3-methyl-10-(4-methyl-1-piperazinyl)-7-oxo-7H-pyrido[1,2,3-de]1,4-benzoxazine-6-carboxylic acid immobilized on an amino-derivatized agarose support by the formation of an amide linkage by reaction with 1-ethyl-3-(3-dimethylaminopropyl) carbodiimide, the first component and the second component being present in the resin at a ratio of about 50:50; and (b) collecting the biological fluid from which pyrogens have been removed.

28. The method of claim 27 wherein the biological fluid is blood.

29. The method of claim 27 wherein the biological fluid is plasma.

30. The method of claim 27 wherein the method removes pyrogens to a final level of below about 0.25 EU/ml.

31. The method of claim 27 wherein the method removes endotoxin.

32. A resin comprising two components: (1) a first component comprising a polymeric support with a multiplicity of ligands comprising a $C_{10}$–$C_{24}$ alkylamino group, the ligands specifically binding endotoxin; and (2) a second component comprising a halogenated quinolone moiety immobilized on an amino-group-containing solid support by the formation of an amide linkage, the first component and the second component being present in the resin at a ratio of from about 20:80 (v/v) to about 80:20 (v/v).

33. The resin of claim 32 wherein the alkylamino group of the first component is a stearylamino group.

34. The resin of claim 32 wherein the polymeric support of the first component is agarose.

35. The resin of claim 32 wherein at least a portion of the ligands of the first component are cross-linked.

36. The resin of claim 35 wherein cross-linking is at the amino moiety of the alkylamino group.

37. The resin of claim 36 wherein the ligands are cross-linked by quaternization with an alkyl group.

38. The resin of claim 37 wherein the ligands are cross-linked by reaction with a dibromoalkanol.

39. The resin of claim 38 wherein the dibromoalkanol is 2,3-dibromopropanol.

40. The resin of claim 32 wherein the polymeric support of the first component is in particle form.

41. The resin of claim 40 wherein the particles are from about 20 microns to about 900 microns in diameter.

42. The resin of claim 41 wherein the particles are from about 60 microns to about 300 microns in diameter.

43. The resin of claim 42 wherein the particles are from about 60 microns to about 100 microns in diameter.

44. The resin of claim 32 wherein the first component comprises an agarose support in particle form of between about 60 microns to about 100 microns in diameter.

45. The resin of claim 32 wherein the polymeric support of the first component is agarose in particle form with a diameter of between about 60 microns to about 100 microns in diameter and the alkylamino group of the first component is a stearylamino group that is cross-linked at at least a portion of the amino moieties of the stearylamino group by reaction with 2,3-dibromopropanol.

46. The resin of claim 32 wherein the halogenated quinolone moiety is of formula (I) wherein $R_1$ is lower alkyl, $R_2$ is lower alkyl, (I)

and X is a halogen selected from the group consisting of fluoro, chloro, bromol iodo.

47. The resin of claim 46 wherein $R_1$ is methyl, $R_2$ is methyl, X is fluoro, and the halogenated quinolone moiety is (±)9-fluoro-2,3-dihydro-3-methyl-10-(4-methyl-1-piperazinyl)-7-oxo-7H-pyrido[1,2,3-de]1,4-benzoxazine-6-carboxylic acid.

48. The resin of claim 46 wherein the amino-containing solid support is amino-derivatized agarose.

49. The resin of claim 46 wherein the halogenated quinolone moiety is immobilized to the amino-containing solid support by reaction with a carbodiimide.

50. The resin of claim 49 wherein the carbodiimide is selected from the group consisting of 1-ethyl-3-(3-dimethylaminopropyl)carbodiimide, 1-cyclohexyl-3-(2-morpholinoethyl)carbodiimide, and N,N'-dicyclohexylcarbodiimide.

51. The resin of claim 50 wherein the carbodiimide is 1-ethyl-3-{3-dimethylaminopropyl) carbodiimide.

52. The resin of claim 32 wherein the first component and the second component are present in a ratio of from about 60:40 (v/v) to about 40:60 (v/v).

53. The resin of claim 52 wherein the first component and the second component are present in a ratio of about 50:50 (v/v).

54. The resin of claim 32 wherein the resin removes pyrogens to a final level of below about 0.25 EU/ml.

55. The resin of claim 32 wherein the resin removes endotoxin.

56. A resin comprising two components: (1) a first component comprising a particulate agarose support with a particle diameter of from about 60 microns to about 100 microns with a multiplicity of ligands comprising a stearylamino group cross-linked by reaction with 2,3-dibromopropanol, the ligands specifically binding endotoxin; and (2) a second component comprising (±)9-fluoro-2,3-dihydro-3-methyl-10-(4-methyl-1-piperazinyl)-7-oxo-7H-pyrido[1,2,3-de]-1,4-benzoxazine-6-carboxylic acid immobilized on an amino-derivatized agarose support by the formation of an amide linkage by reaction with 1-ethyl-3-(3-dimethylaminopropyl) carbodiimide, the first component and the second component being present in the resin at a ratio of about 50:50.

57. The resin of claim 56 wherein the resin removes pyrogens to a final level of below about 0.25 EU/ml.

58. The resin of claim 56 wherein the resin removes endotoxin.

59. A cartridge for removal of pyrogens comprising:
 (a) a housing for holding a resin, the housing having first and second ends;
 (b) the resin of claim 32;
 (c) an inlet attached to the first end of the housing for allowing a biological fluid selected from the group consisting of blood and plasma to flow into the housing; and
 (d) an outlet attached to the second end of the housing for allowing the biological fluid from which pyrogens have been removed to flow out of the housing.

60. The cartridge of claim 59 wherein the cartridge removes pyrogens to a final level of below about 0.25 EU/ml.

61. The cartridge of claim 59 wherein the cartridge removes endotoxin.

62. An assembly comprising a plurality of the cartridges of claim 59 connected in series so that the outlet of each cartridge is connected to the inlet of the next cartridge.

* * * * *